United States Patent [19]

Honigs et al.

[11] Patent Number: 4,847,066

[45] Date of Patent: Jul. 11, 1989

[54] METHOD OF TREATING A CONSUMABLE PRODUCT AND PACKAGING FOR CONSUMABLE PRODUCTS TO INDICATE THE PRESENCE OF CONTAMINATION

[75] Inventors: David E. Honigs, Brier; Jonathan H. Perkins; Bradley J. Tenge, both of Seattle, all of Wash.

[73] Assignee: Board of Regents of the University of Washington, Seattle, Wash.

[21] Appl. No.: 937,839

[22] Filed: Feb. 2, 1987

Related U.S. Application Data

[62] Division of Ser. No. 886,528, Jul. 16, 1986.

[51] Int. Cl.$^4$ .............................................. G01N 31/22
[52] U.S. Cl. ..................... 424/7.1; 424/439; 424/451; 424/464; 424/484; 426/231; 426/531; 436/1; 436/2; 436/20
[58] Field of Search ............ 426/87, 88, 383, 531, 426/231, 328; 436/1, 2, 20; 99/493; 116/206, 335; 424/7.1, 439, 451, 454, 464, 484

[56] References Cited

U.S. PATENT DOCUMENTS

| | | | |
|---|---|---|---|
| 2,063,245 | 12/1936 | Haeseler | 426/87 |
| 2,626,855 | 1/1953 | Hand | 426/87 X |
| 2,712,997 | 7/1955 | Cooley | 426/231 |
| 3,438,781 | 4/1969 | MacMillan | 426/328 X |
| 4,421,858 | 12/1983 | Jackson | 426/231 X |

FOREIGN PATENT DOCUMENTS 1418332 12/1975 United Kingdom ............... 426/231

*Primary Examiner*—Barry S. Richman
*Assistant Examiner*—Jill Johnston
*Attorney, Agent, or Firm*—Christensen, O'Connor, Johnson & Kindness

[57] ABSTRACT

A method is described for treating consumable products, such as foods, drugs or dietary supplements, for example drugs enclosed in capsules, to detect contamination. A colorimetric indicator, which can react with a contaminating substance such as cyanide, is incorporated into the consumable product or the packaging for the product. When the indicator comes in contact with the contaminating substance, a readily detectable color signal is produced.

53 Claims, No Drawings

METHOD OF TREATING A CONSUMABLE PRODUCT AND PACKAGING FOR CONSUMABLE PRODUCTS TO INDICATE THE PRESENCE OF CONTAMINATION

This is a divisional of the prior application Ser. No. 886,528, filed July 16, 1986, the benefit of the filing dates of which are hereby claimed under 35 USC 120.

FIELD OF THE INVENTION

This invention relates to a method of treating a consumable product and packaging for such products to indicate the presence of contamination, and to products and packaging containing a contamination indicator.

BACKGROUND OF THE INVENTION

The presence of undesirable contamination, for example, toxins such as cyanide compounds, in products intended for human consumption has caused increased concern among pharmaceutical and food product manufacturers as well as the general public because of the potential for serious illness and even death as a result of ingesting contaminated products. In many cases, it is not possible to detect the presence of the contaminating substance which may be dangerous even in small quantities, because the content of the product, for example, a powdered form of drug within a capsule, or a solid or liquid food product, masks the presence of the contaminant.

Although individual food items may be presently tested for contamination, as described in the Code of Federal Regulations (CFR), Title 21, Subchapter B, parts 100-199, most drugs and dietary supplements, such as vitamins, are packaged in quantities of small, individual units, for example, as capsules within a bottle, making individual screening prior to consumption economically unfeasible.

Accordingly, it is an object of the present invention to provide a method to treat various consumable products, including drugs, dietary supplements and foods, and packaging for such products, to detect contamination using an indicator which permits easy detection of contamination.

A further object of this invention is to provide consumable products and packaging for consumable products containing such indicators.

Other objects and advantages of the present invention will become apparent by considering the Detailed Description and examples which follow.

SUMMARY OF THE INVENTION

The invention sets forth a method of treating a product such as a food, drug or dietary supplement, intended for consumption or ingestion, to indicate the presence of a contaminating substance or toxicant. A colorimetric indicator, preferably an iron-containing compound, capable of reacting with a contaminating substance composed of a compound, such as a cyanide compound, is incorporated into a consumable product. The indicator reacts with contaminants, including cyanide compounds and those containing $-NH_3^+$, $-NH_2$ and $-O^{-2}$ groups, to produce an easily detectable color signal indicating the presence of contamination. The indicator may be incorporated during processing of the product, or afterwards as a coating, and may also be incorporated into the external packaging of the product.

DETAILED DESCRIPTION OF THE INVENTION

The present invention describes a method for treating a consumable or ingestible product using a colorimetric indicator capable of reacting with the contaminant or toxicant to produce a color indicating the presence of contamination in the product. Consumable or ingestible products with respect to which the present invention may be employed include: foods (e.g., dry, freeze-dried, concentrates, solid and liquid); food ingredients (e.g., spices, flavorings, salts, flour, baking powder and baking soda; drugs, including those contained in a capsule and in liquid form; and, dietary supplements, such as vitamins. The contamination indicator may be incorporated into the consumable product by several different methods. For use in a solid or dry food product, for example, the indicator may simply be mixed with the other components of the food product during processing or added to the food packaging. The indicator may be added directly to a liquid product, such as milk during or after processing. For incorporation into a drug or dietary supplement, for example, a gelatin capsule containing a drug or vitamin, the indicator may be physically absorbed onto the surface of the gelatin capsule by soaking the capsule in the solution, or the indicator may be added during the formation of the gelatin capsule to produce a capsule containing the indicator. The indicator also may be combined with the drug or vitamin components during preparation. The indicator also may be used as a coating on the surface of a drug or food product.

In another aspect of the invention, the colorimetric indicator as described herein, may be incorporated into the external packaging of the consumable product, to indicate the presence of a potentially harmful contaminating substance in the consumable product. For example, wax is a common component of the packaging of many foods, including milk, jello and cereal. The colorimetric indicator may be mixed into the wax during processing and used to coat a container made of paper or other material for holding the consumable product. The container is filled with the product and if the product contains a contaminant the contaminant will react with a colorimetric indicator to produce a color so that the manufacturer or purchaser can readily detect the presence of the contamination by viewing the container. The colorimetric indicator may also be incorporated into other components of packaging during or after manufacture of the particular package using technology which is known to those skilled in the art.

A colorimetric indicator as used herein means a compound or mixture of compounds containing a metal element including iron (Fe), silver (Ag), zinc (Zn), manganese (Mn), copper (Cu) and molybdenum, (Mo), or organic dyes such as ninhydrin or azo dyes, which can produce a characteristic color when reacted with a corresponding analyte (here, a contaminating substance). Reactive pairs of colorimetric indicators and corresponding contaminating substances reactive with the indicators include, but are not limited to, those depicted in Table I. The colors characteristically generated by these pairs are also listed.

TABLE I

| (A) Colorimetric Indicator | (B) Contaminant (Reacting Group)[c] | (C) Color Produced By Reaction of (A) and (B) |
|---|---|---|
| 1. Iron (Fe III)[a] | Mercuric acetate (acetate $CH_3COO^-$) | Dark shade of Reddish Brown |
| 2. Iron (Fe II) | Barium carbonate (carbonate $CO_3^{-2}$) | White |
| 3. Iron (Fe II) | Gallium citrate (citrate $C_6H_6O_7^{-2}$) | White |
| 4. Iron (Fe III) | Gallium citrate (citrate $C_6H_5O_7^{-3}$) | Green |
| 5. Iron (Fe III) | Potassium Cyanide (cyanate CN) | Blue |
| 6. Iron (Fe II) | Formic acid-dithiobis (thio-, 0,0-diethyl-ester (formate $HCO_2^-$) | Green |
| 7. Iron (Fe III) | Formic acid-dithiobis (thio-, 0,0-diethyl-ester (formate $HCO_2^-$) | Red |
| 8. Iron (Fe II) | Chloro-fumeric acid (fumarate $C_4H_2O_4^{-2}$) | Reddish Brown |
| 9. Iron (Fe II) | Antimony-V-Sodium Gluconate (gluconate $C_6H_{11}O_7^-$) | Yellow |
| 10. Iron (Fe II) | Mercury Nitrate (nitrate $NO_3^-$) | Green |
| 11. Iron (Fe III) | Mercury I Nitrate (nitrate $NO_3^-$) | Violet |
| 12. Iron (Fe II) | Hydrogen peroxide (oxo $O^{-2}$) | Various Colors |
| 13. Iron (Fe III) | Mercury II Sulfate (sulfate $SO_4^{-2}$) | Yellow |
| 14. Zinc ($Zn^\circ$)[b] | Strychnine (alkaloid) | Rose Red |
| 15. Manganese ($Mn^{+7}$)[d] | Strychnine (alkaloid) | Purplish |
| 16. Copper ($Cu^\circ$)[e] | Arsenic (arsenic As) | Black or Brown |
| 17. Molybdenum ($Mo^{+6}$)[e] | Arsenic (arsenic As) | Deep Blue |
| 18. Silver ($Ag^+$)[f] | Cyanide (cyanate $CN^-$) | White |

[a]Reactions for Iron from "Iron Compounds," Encyclopedia of Chemical Technology, Vol. 13, 3rd. Ed., Wiley-Interscience, New York (1981), incorporated by reference herein.
[b]Reactions for zinc from Chem. Abstracts, 5, p. 564[7] (1911), incorporated by reference herein.
[c]Contaminants from Registry of Toxic Effects of Chemical Substances, 1976 and 1980 editions, U.S. Department of Health and Human Services.
[d]Reactions for manganese from Chem. Abstracts, 7, p. 208[9] (1913), incorporated by reference herein.
[e]Reactions for copper and molybdenum from Analytical Chemistry of Industrial Poisons, Hazards and Solvents, M. B. Jacobs, Interscience Pub., New York (1941), incorporated by reference herein.
[f]Reaction for silver from Allen's Commercial Organic Analysis, 5th Ed., P. Blackinston's Son Co., Inc., Philadelphia (1930), incorporated by reference herein.

Other colorimetric indicators may be selected to react with additional contaminating substances, such as those reacting pairs described in *Poisoning By Drugs and Chemicals, Plants and Animals*, by Peter Cooper, Yearbook Medical Publishers, Inc., Chicago, 3rd Ed., (1974), incorporated by reference herein.

Consumable products containing the contamination indicator may be consumed without ill effects and, in some cases, with beneficial effects. To carry out the present invention, preferably, iron-containing compounds are used to make saturated solutions which may be diluted and then incorporated into the consumable product. When the iron-containing compound comes in contact with a contaminant, such as a cyanide compound or a compound containing, for example, an ammonium ($-NH_3^+$), amine ($-NH_2$) or oxo ($-O^{-2}$) group, a characteristic color is produced. Of particular interest are cyanide compounds, such as potassium cyanide (KCN), sodium cyanide (NaCN), and hydrogen cyanide (HCN).

The color signal produced by the reaction of the colorimetric indicator and the contaminating substance may be detected simply by observing the product or by using ultraviolet irradiation to visualize the signal. The invention is set forth in greater detail in the following description and examples which follow.

The colorimetric indicator chosen for indicating the presence of contamination in the consumable product must be capable of reacting with the particular contaminant so as to result in an easily detectable reaction. Preferred substances to indicate contamination are those which produce a color when reacted, such as iron-containing compounds, including trivalent iron chloride ($FeCl_3$, Fe III) and divalent iron sulfate ($FeSO_4$, Fe II), and mixtures of the two compounds. Thus, $FeCl_3$ and $FeSO_4$ each may be dissolved in water to form two separate, saturated solutions. The solutions are mixed together and then diluted, for example, with glycerin. Alternatively, $FeSO_4$ may be used alone to indicate contamination. A saturated solution of $FeSO_4$ may be mixed with glycerin and added to a consumable product as described for the mixture of $FeCl_3$ and $FeSO_4$. Contact of the iron-containing substance with a contaminant, such as a cyanide compound, produces an easily visualized color signal indicating the presence of the contaminant. The use of such iron-containing compounds to detect contamination may yield a range of reactions with different colors depending upon the particular contaminant being detected. For example, a dark blue color ("Prussian blue") is produced by reaction of a mixture of $FeCl_3$ and $FeSO_4$ with potassium cyanide (KCN). When $FeSO_4$ alone is reacted with KCN a reddish-brown color results. While contaminants containing other active groups may be detected using the iron-containing compounds, the color reaction may be weaker than that with a cyanide compound and, thus, more difficult to detect.

In addition to the foregoing, compounds which produce fluorescence or change their inherent fluorescence when reacted with a contaminating substance may be used, and the presence of the contaminant revealed using ultraviolet irradiation.

Iron (in the form of Fe°, Fe II and Fe III) is typically used as a dietary supplement, for example, for fortifying milk, cereals or alone, and may be taken in amounts up to 18 milligrams of Fe per day without harmful side effects, per the Recommended Dietary Allowances, Food and Nutrition Board, National Academy of Sciences, National Research Council, Washington, D.C., (1980). Therefore, the use of iron-containing compounds to indicate product contamination will not harm the consumer, and may, in fact have beneficial effects as a dietary supplement. Of course, the total amount of indicator present in the product should not be large enough to pose a health hazard.

It is preferable when incorporating the indicator into the consumable product or packaging which may mask the color reaction. For example, use of a mixture $FeCl_3$ and $FeSO_4$ produces a Prussian blue color in response to the presence of KCN. Thus, it may be desirable to eliminate blue coloring from consumable products or packaging into or onto which a mixture of these iron-containing compounds is incorporated. Similarly, use of $FeSO_4$ produces a reddish-brown coloring upon contact with KCN. When the indicator substance is used in drugs, for example, gelatin capsules, transparent gelatin capsules are preferable to permit easy viewing of the color reaction in the presence of the contaminant. A pharmaceutical manufacturer may wish to eliminate certain colors, for example, blues and reds from the components of the drugs or dietary supplements, including those enclosed in capsules, or from the packaging to prevent a masking effect.

The following examples are presented to illustrate the present invention and to assist one of ordinary skill in making and using the same. The examples are not intended in any way to otherwise limit the scope of the disclosure or the protection granted by the Letters Patent hereon.

EXAMPLE I

Investigation of Color Generated Using Iron Containing Compounds and KCN

Two saturated solutions of iron were prepared, a first solution in the form of $FeCl_3 \cdot 6H_2O$ (J.T. Baker, Phillipsburg, NJ), containing approximately 100-150 g $FeCl_3$ in 1 liter of water, and a second solution in the form of $FeSO_4 \cdot 7H_2O$ (Aldrich Chemical Co., Milwaukie, WI), containing approximately 150-200 g of $FeSO_4$ in 1 liter of water. The two saturated solutions were mixed together using various ratios of Fe III and Fe II, (from 1:1 to 50:1) and reacted with approximately 1 mg of potassium cyanide (KCN) (Alfa Products, Danvers, ME) to obtain a suitable reaction color. Only a trace (much less than 1 mg) of KCN is required to produce a color reaction. Approximately 14 mg of KCN is the $LD_{LO}$ (low lethal dose) for a person weighing approximately 50 kg. *Registry of Toxic Effects of Chemical Substances,* U.S. Dept. of Health, Education and Welfare, Center for Disease Control, National Institute for Occupational Safety and Health, Rockville, MD (1976).

When saturated Fe II was added to approximately 1 mg of KCN, a rusty-brown color resulted. When saturated Fe III was used alone and reacted with approximately 1 mg KCN, a mottled rusty color resulted. Using a 1:1 ratio of saturated Fe II to Fe III, approximately 1 mg of KCN produced a greenish color with brownish clumps. The ratio of Fe III to Fe II was increased to 2:1 and the resulting color was olive-green. The color produced became darker and darker as the ratio of Fe III to Fe II increased, until at a ratio of 50:1 the color became a dark blue.

EXAMPLE II

Detection of KCN in Capsules Using Iron Chloride and Iron Sulfate

Solutions containing Fe III and Fe II in 1) a 1:1 ratio and 2) a 50:1 ratio were each diluted to a 1:1 ratio by volume using glycerin (JT Baker Chemical Co., Phillipsburg, N.J.), and were mixed thoroughly. Capsules from: (a) Anacin 3 ® (opaque, yellow and white capsules); (b) acetaminophen capsules (generic); and, (c) clear capsules from calcium supplements (Twin Lab Oyster Shell Calcium Caps, Ronkonkoma, N.Y.) were each dipped in the iron glycerin-solution and then wiped dry within one minute using a chemwipe tissue. Two capsules were loaded with aspirin (Anacin ®), and two others with approximately 600 mg KCN. The clear capsules containing KCN on their inner surface showed brown to blue spots within 5 minutes, as did the white and yellow opaque capsules.

To improve the incorporation of the iron-containing mixture into the capsules, clear capsules from the calcium supplements were soaked for about 5 minutes in a 50:1 Fe III to Fe II mixture, then diluted with an equal amount of glycerin. The capsules were air dried. The amount of iron adsorbed onto the capsule using this process was approximately 1.5 mg iron (Fe). After drying, some of the capsules were filled either with acetaminophen or with approximately 600 mg KCN. Some of the capsules that were loaded first with acetaminophen, were then emptied out and refilled with KCN to simulate a capsule tampering event, and to demonstrate that a capsule treated with iron would remain reactive after being packed with aspirin. Those capsules containing KCN showed reddish-brown to blue spots within one hour of contact with the KCN, with the spots being smaller and more uniform than observed when the capsules were wiped dry. No reaction was observed with the acetminophen. The capsules that were first loaded with acetaminophen and then cyanide showed color spots similar to those capsules loaded with 600 mg of pure KCN.

EXAMPLE III

Detection of Strychnine Contamination Using Zinc (Zn)

A suspension of zinc metal (in the form of Zn ®) in water is made and diluted using glycerin in an acidic (pH less than 7) solution. Gelatin capsules for containing drugs or vitamins are soaked in the zinc-glycerin to adsorb the zinc onto the capsules. When the capsules are filled with strychnine, a rose red color appears.

EXAMPLE IV

Detection of Strychnine Contamination Using Potassium Permanganate ($KMnO_4$)

A solution of $KMnO_4$ in water is made and diluted with a glycerin solution. Glycerin capsules for containing drugs or vitamins are soaked in the $KMnO_4$-glycerin solution to adsorb the $KMnO_4$ onto the capsules. When the capsules are filled with strychnine, a purplish color results. The $KMnO_4$-glycerin capsules will also detect other contaminating alkaloid compounds including drugs such as cocaine and heroin, and natural alkaloid toxins, such as solanine, contained in potatoes, tomatoes, and sugarbeets, and discorine contained in yams. Kunitz, M., *J. Gen. Physiol.*, 30, p.311 (1947).

EXAMPLE V

Detection of Arsenic Contamination Using Copper ($Cu^\circ$)

Solid copper in the form of $Cu^\circ$ is used to form a suspension in water. Glycerin is added to the suspension. Gelatin capsules for containing drugs or vitamins are soaked in the copper suspension to adsorb copper onto the capsules. When arsenic (As) is placed in the capsule, a black or brownish color results.

EXAMPLE VI

Detection of Arsenic Contamination Using Ammonium Molybdate (($NH_4)_2MoO_4$)

A saturated solution of ammonium molybdate (($NH_4)_2MoO_4$) in water is made. The solution is diluted with glycerin and used to soak gelatin capsules to adsorb $MoO_4^{-2}$ onto the capsules. When arsenic is placed in the capsules, an intense blue color appears.

These results demonstrate that various colorimetric indicators may be incorporated into a consumable product such as a drug-containing gelatin capsule, to indicate the presence of a contaminant, such as a cyanide compound. The colorimetric indicator reacts with the contaminant to produce a readily visualized, color reaction.

While the present invention has been described in conjunction with the preferred embodiments, one of ordinary skill, having read the foregoing specification, will be able to effect various changes, substitutions of equivalents, and alterations to the methods set forth herein. It is, therefore, intended that the protection granted by Letters Patent hereon be limited only by the appended claims and equivalents thereof.

The embodiments of the invention in which an exclusive property or privilege is claimed are defined as follows:

1. A method of treating an ingestible product intended for human consumption to indicate the presence of a toxicant comprising:
incorporating into said product a colorimetric indicator in an amount that is non-toxic and capable of reacting with said toxicant to generate a detectable signal.

2. The method according to claim 1, wherein said toxicant contains a reactive group selected from the group consisting of cyanate ($-CN^-$), ammonium ($-NH_3^+$), amine ($-NH_2$), oxo ($-O^{-2}$), acetate ($-CH_3COO^-$), carbonate ($-CO_3^-$), citrate ($-C_6H_6O_7^{-2}$, $-C_6H_5O_7^3$), formate ($-HCO_2$), fumarate ($-C_4H_2O_4^{-2}$), gluconate ($-C_6H_{11}O_7^-$), nitrate ($-NO_3^-$), sulfate ($-SO_4^{-2}$), arsenic (As), and alkaloids.

3. The method according to claim 2, wherein said colorimetric indicator is a compound containing a metal element.

4. The method according to claim 3, wherein said metal element is selected from the group consisting of Fe II, Fe III, $Fe^\circ$, $Zn^\circ$, $Ag^+$, $Mn^{+7}$, $Mo^{+6}$, and $Cu^\circ$.

5. The method according to claim 2, wherein said colorimetric indicator contains an organic dye compound.

6. The method according to claim 5, wherein said colorimetric indicator contains a ninhydrin compound.

7. The method according to claim 5, wherein said colorimetric indicator contains an azo dye compound.

8. The method according to claim 1, wherein said toxicant comprises a cyanide compound selected from the group consisting of KCN, HCN, and NaCN.

9. The method according to claim 1, wherein said toxicant is KCN.

10. The method according to claim 1, wherein said product intended for human consumption is selected from the group consisting of drugs, drug complexes, foods, food ingredients and dietary supplements.

11. The method according to claim 10, wherein said product intended for human consumption is a drug-containing capsule.

12. The method according to claim 11, wherein the capsule is composed essentially of gelatin.

13. The method according to claim 11, wherein said step of incorporating comprises physically adsorbing said colorimetric indicator onto the capsule by soaking the capsule in a solution of said colorimetric indicator.

14. The method according to claim 11, wherein said step of incorporating comprises mixing said colorimetric indicator with the components of the capsule during preparation of the capsule, to produce a capsule containing said colorimetric indicator.

15. The method according to claim 1, wherein said product is a food, and the step of incorporating comprises mixing said colorimetric indicator with components of the food, during preparation of the food.

16. The method according to claim 1, wherein said product is a food and the step of incorporating comprises coating the food with said colorimetric indicactor.

17. The method according to claim 1, wherein said product is a liquid and the step of incorporating comprises mixing said colorimetric indicator into the liquid.

18. The method according to claim 1, wherein said colorimetric indicator contains an iron-containing compound.

19. The method according to claim 18, wherein said colorimetric indicator contains one or more reactive groups selected from the group consisting of $FeCl_3$, $FeSO_4$, and mixtures thereof.

20. The method according to claim 18, wherein said colorimetric indicator is a mixture of compounds containing Fe (III) and Fe (II).

21. The method according to claim 18, wherein glycerin is added to a solution of said colorimetric indicator capable of reacting with the contaminating substance.

22. The method according to claim 1, wherein said detectable signal comprises a color generated by the reaction between the contaminating substance and said colorimetric indicator capable of reacting with the contaminating substance.

23. The method according to claim 22, wherein the color is detectable using ultraviolet irradiation.

24. The method according to claim 22, wherein the color is detectable by visual observation.

25. The method according to claim 24, wherein said toxicant is KCN and said colorimetric indicator is a mixture of $FeCl_3$ and $FeSO_4$.

26. The method according to claim 24, wherein said toxicant is KCN and said colorimetric indicator is $FeSO_4$.

27. The method according to claim 1, wherein said colorimetric indicator is a zinc-containing compound and said toxicant contains an alkaloid compound.

28. The method according to claim 27, wherein said toxicant is strychnine.

29. The method according to claim 1, wherein said colorimetric indicator is a manganese-containing compound and said toxicant contains an alkaloid compound.

30. The method according to claim 29, wherein said toxicant is strychnine.

31. The method according to claim 1, wherein said colorimetric indicator is a copper-containing compound and said toxicant is arsenic.

32. The method according to claim 1, wherein said colorimetric indicator is a molybdenum-containing compound and said toxicant is arsenic.

33. A product intended for human consumption, comprising an ingestible product containing a colorimetric indicator in an amount that is ingestible, nontoxic and capable of reacting with a toxicant to generate a detectable signal indicating the presence of said toxicant.

34. The product according to claim 33, comprising a drug-containing capsule.

35. The product according to claim 33, comprising a capsule containing a dietary supplement.

36. The product according to claim 33, wherein said detectable signal is a color detectable by visual observation.

37. The product according to claim 33, wherein said detectable signal is a color detectable by using ultraviolet irradiation.

38. The product according to claim 33, wherein said colorimetric indicator contains an iron-containing compound, and said toxicant is a cyanide compound.

39. The product according to claim 38, wherein said colorimetric indicator comprises a mixture of $FeCl_3$ and $FeSO_4$ and said cyanide compound is KCN.

40. The product according to claim 38, wherein said colorimetric indicator is $FeSO_4$ and said cyanide compound is KCN.

41. The product according to claim 33, wherein said toxicant contains a reactive group selected from the group consisting of cyanate ($-CN^-$), ammonium ($-NH_3^+$), amine ($-NH_2$), oxo ($-O^{-2}$), acetate ($-CH_3COO^-$), carbonate ($-CO_3^-$), citrate ($-C_6H_6O_7^{-2}$, $-C_6H_5O_7^{-3}$), formate ($-HCO_2^-$), fumarate ($-C_4H_2O_4^{-2}$), gluconate ($-C_6H_{11}O_7^-$), nitrate ($-NO_3^-$), sulfate ($-SO_4^{-2}$), arsenic (As), and alkaloids.

42. The product according to claim 41, wherein said colorimetric indicator is a compound containing a metal element.

43. The product according to claim 42, wherein said metal element is selected from the group consisting of Fe II, Fe III, $Fe°$, $Zn°$, $Ag^+$, $Mn^{+7}$, $Mo^{+6}$ and $Cu°$.

44. The product according to claim 41, wherein said colorimetric indicator contains an organic dye compound.

45. The product according to claim 44, wherein said colorimetric indicator contains a ninhydrin compound.

46. The product according to claim 44, wherein said colorimetric indicator contains an azo dye compound.

47. The product according to claim 33, wherein said colorimetric indicator is a zinc-containing compound and said toxicant contains an alkaloid compound.

48. The product according to claim 47, wherein said contaminating substance is strychnine.

49. The product according to claim 33, wherein said colorimetric indicator is a manganese-containing compound and said contaminating substance contains an alkaloid compound.

50. The product according to claim 49, wherein said contaminating substance is strychnine.

51. The product according to claim 33, wherein said colorimetric indicator is a copper-containing compound and said contaminating substance is arsenic.

52. The product according to claim 33, wherein said colorimetric indicator is a molybdenum-containing compound and said contamination substance is arsenic.

53. A method for treating an ingestible product intended for human comsumption to indicate the presence of a toxicant, comprising:
incorporating into said product a colorimetric indicator in an amount that is nontoxic and capable of reacting with said toxicant to generate a detectable signal is a substantially dry environment.

* * * * *

UNITED STATES PATENT AND TRADEMARK OFFICE
CERTIFICATE OF CORRECTION

PATENT NO. : 4,847,066

DATED : July 11, 1989

INVENTOR(S) : Honigs et al.

It is certified that error appears in the above-identified patent and that said Letters Patent is hereby corrected as shown below:

Column 1, line 3: "dates" should be --date--

Column 1, line 3: "are" should be --is--

Column 2, line 16: "soda;" should be --soda);--

Column 3, lines 14-15: "0.0" should be --0,0--

Column 3, lines 21-22: "Mercury Nitrate" should be --Mercury I Nitrate--

Column 5, line 17: after "packaging" insert --to eliminate or reduce components in the consumable product or packaging--

Column 6, line 51: "Zn®" should be --Zn°--

Column 7, line 57: "$(-C_4H_2O_4-2)$" should be --$(-C_4H_2O_4^{-2})$--

Column 8, line 17: "claim II" should be --claim 11--

Column 10, line 1: "(-0-2)," should be --$(-O^{-2})$,--

Column 10, line 12: "Mn+7, Mo+6" should be --$Mn^{+7}$, $Mo^{+6}$,--

Column 10, line 36: "contamination" should be --contaminating--

UNITED STATES PATENT AND TRADEMARK OFFICE
CERTIFICATE OF CORRECTION

PATENT NO. : 4,847,066

DATED : July 11, 1989

INVENTOR(S) : Honigs et al.

It is certified that error appears in the above-identified patent and that said Letters Patent is hereby corrected as shown below:

Column 10, line 43: "is" should be --in--.

Signed and Sealed this

Twelfth Day of June, 1990

Attest:

HARRY F. MANBECK, JR.

*Attesting Officer*      *Commissioner of Patents and Trademarks*